US012440393B2

(12) United States Patent
Khan et al.

(10) Patent No.: US 12,440,393 B2
(45) Date of Patent: Oct. 14, 2025

(54) TAMPON AND APPLICATOR ASSEMBLY WITH ADVANTAGEOUSLY-SHAPED GRIPPING PORTION

(71) Applicant: The Procter & Gamble Company, Cincinnati, OH (US)

(72) Inventors: Ayub Ibrahim Khan, Cincinnati, OH (US); Naomi Ruth Nelson, Cincinnati, OH (US); Eric Mitchell Schickli, Cincinnati, OH (US); Kerry Lloyd Weaver, Florence, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 636 days.

(21) Appl. No.: 16/824,934

(22) Filed: Mar. 20, 2020

(65) Prior Publication Data

US 2021/0290448 A1 Sep. 23, 2021

(51) Int. Cl.

*A61F 13/26* (2006.01)
*A61F 13/15* (2006.01)
*A61F 13/20* (2006.01)
*A61F 13/551* (2006.01)

(52) U.S. Cl.

CPC ........ *A61F 13/266* (2013.01); *A61F 13/2097* (2013.01); *A61F 13/5518* (2013.01); *A61F 13/55185* (2013.01); *A61F 2013/1539* (2013.01)

(58) Field of Classification Search

CPC .......... A61F 13/26; A61F 13/38; A61F 13/36; A61F 13/226; A61F 13/2097; A61F 13/5518; A61F 13/55185; A61F 2013/1539; A61F 5/44; A61F 6/08

See application file for complete search history.

(56) References Cited

U.S. PATENT DOCUMENTS 5,533,966 A * 7/1996 Schoelling ............ A61F 13/263 604/18
6,258,075 B1 7/2001 Taylor
6,554,814 B1 4/2003 Agyapong
6,610,025 B2 8/2003 Berg
(Continued)

FOREIGN PATENT DOCUMENTS

WO WO-2019068351 A1 * 4/2019 ............. A61F 13/26

*Primary Examiner* — Nicholas J. Weiss
*Assistant Examiner* — Gabriella E Burnette
(74) *Attorney, Agent, or Firm* — Sarah M. DeCristofaro

(57) ABSTRACT

A tampon product including a tampon within an applicator assembly is disclosed. The applicator assembly includes a barrel portion joined to a gripping portion, imparted with features that improve utility and convenience for the user. In one example the gripping portion has a rearward edge defining differing first and second lengths. In another example the gripping portion has a lateral outer cross section profile that is substantially oval-shaped, ovoid-shaped, elliptical or stadium-shaped and has major and minor axes, each perpendicular to a longitudinal axis, along first and second lateral perpendicular directions, wherein following absorption of fluid the tampon will expand laterally to a first lateral dimension to a greatest extent along a first lateral direction, and to a lesser second lateral dimension along a second lateral direction 90 degrees from the first lateral direction, wherein the first lateral direction is substantially parallel to one of the major and minor axes.

9 Claims, 3 Drawing Sheets

(56) References Cited

U.S. PATENT DOCUMENTS

| | | | | |
|---|---|---|---|---|
| 6,652,477 | B2 | 11/2003 | Karapasha | |
| 6,730,057 | B2 | 5/2004 | Zhao | |
| 6,824,536 | B2 | 11/2004 | Randall | |
| 6,840,927 | B2 | 1/2005 | Hasse | |
| 6,932,805 | B2 | 8/2005 | Domeier | |
| 6,939,340 | B1 | 9/2005 | Berges | |
| 6,953,456 | B2 | 10/2005 | Fuchs | |
| 7,066,870 | B2 | 6/2006 | Fedyk | |
| 7,081,110 | B2 | 7/2006 | Karapasha | |
| 7,166,101 | B2 | 1/2007 | Denti | |
| 7,549,982 | B2 | 6/2009 | Carlin | |
| 8,029,485 | B2 | 10/2011 | Jensen | |
| 8,075,512 | B2 | 12/2011 | Sargent | |
| 8,216,202 | B2 | 7/2012 | Minoguchi | |
| 8,303,558 | B2 | 11/2012 | Fedyk | |
| 8,449,491 | B2 | 5/2013 | Hasse | |
| 8,597,267 | B2 | 12/2013 | Noel | |
| 8,684,987 | B2 | 4/2014 | Hasse | |
| 2008/0195030 | A1* | 8/2008 | Gann | A61F 13/26 604/15 |
| 2008/0243046 | A1* | 10/2008 | Cettina | A61F 13/266 604/15 |
| 2011/0190685 | A1* | 8/2011 | Arora | A61F 6/12 604/14 |
| 2012/0204410 | A1* | 8/2012 | Mastalish | A61F 13/55185 29/505 |
| 2015/0060317 | A1* | 3/2015 | De Soto-Burt | A61F 13/26 206/370 |

* cited by examiner

TAMPON AND APPLICATOR ASSEMBLY WITH ADVANTAGEOUSLY-SHAPED GRIPPING PORTION

BACKGROUND

Tampons have been used by women for many years to contain and absorb menstrual fluid during menses, to avoid soiling undergarments, outer clothing, bedding, etc. The typical currently marketed tampon is formed of an absorbent structure that may include absorbent material(s) such as rayon and cotton. The structure is typically formed and compressed into a cylindrical shape about the size of a small finger, having a forward/insertion end and a rearward end, and configured to be easily inserted into suitable position in the vaginal cavity and then to expand therewithin as it is contacted by and absorbs menstrual fluid, and swells with the absorbed fluid. Typically, a tampon will include a securely attached withdrawal cord extending from its rearward end, of a length sufficient to extend down the vaginal canal and outside the vagina during and after insertion of the tampon into suitable position. After a desired length of time following insertion the user may pull the cord to withdraw and remove the tampon.

Some users prefer tampons that are unaccompanied by applicators, preferring to insert a tampon using a finger to directly ("digitally") contact and manipulate the tampon into suitable position within the vaginal cavity.

Other users, however, prefer a tampon that is provided with an applicator assembly that houses the new tampon prior to use, and facilitates insertion without the need to insert a finger into the vaginal canal. The typical applicator assembly includes a hollow barrel portion, often of a substantially cylindrical shape and having a forward end and a rearward end, within which the new tampon is contained. The applicator assembly also typically includes an ejection plunger that is disposed in contact with the rearward end of the tampon inside the barrel portion, and extends rearwardly from the rearward end of the barrel portion, and is configured to slide coaxially into the rearward end of the barrel portion and thereby provide a mechanism by which the user can push the tampon out the forward end of the barrel portion. The forward end of the barrel portion may be rounded or tapered to a gently rounded but openable tip to facilitate insertion. An openable configuration may be formed of a group of radially-arranged flexible petals that are rounded and curved inwardly at their distal ends toward the longitudinal axis of the applicator assembly, to close off the forward end and contain the new tampon, but flex radially outwardly under contact and forward pressure by the tampon, to open and allow the tampon to be urged forward and out of the forward end of the barrel portion when the ejection plunger is pushed by the user.

Applicator assemblies and their component parts may be formed of various materials and have a variety of design features, to enhance the user experience and facilitate cost-effective manufacture. Any improvements to features that further either of both of these objectives may provide the manufacturer/seller of tampons with applicator assemblies a competitive advantage.

DESCRIPTION OF EXAMPLES

Definitions

As used herein "applicator assembly" refers to a device or implement that houses, and facilitates the insertion and placement of, a tampon or other device into an external orifice, such as the vagina. Non-limiting specific examples of such include any known applicator assembly that may be used for insertion of a tampon, such as telescoping tube and plunger assemblies.

"Substantially parallel," with respect to two coplanar lines of direction, describes lines of direction that are precisely parallel (never intersect), and lines of direction that intersect and thereby deviate from precisely parallel, by no more than 10 degrees.

"Substantially perpendicular," with respect to two coplanar lines of direction, describes lines of direction that are precisely perpendicular (intersect at an angle of 90 degrees), and lines of direction that deviate from precisely perpendicular by no more than 10 degrees (i.e., intersect at an angle from 80 degrees to 100 degrees).

As used herein, "substantially cylindrical" refers to and includes the outer shape of a cylinder, but also includes shapes such as slightly oblate or slightly flattened cylinders, slightly curved cylinders, and shapes which have diameters and/or cross-sectional areas that vary slightly along their lengths, wherein minor deviation from a precise cylindrical shape does not compromise product manufacturability, function or utility.

Figures 1A, 1B, 1C:
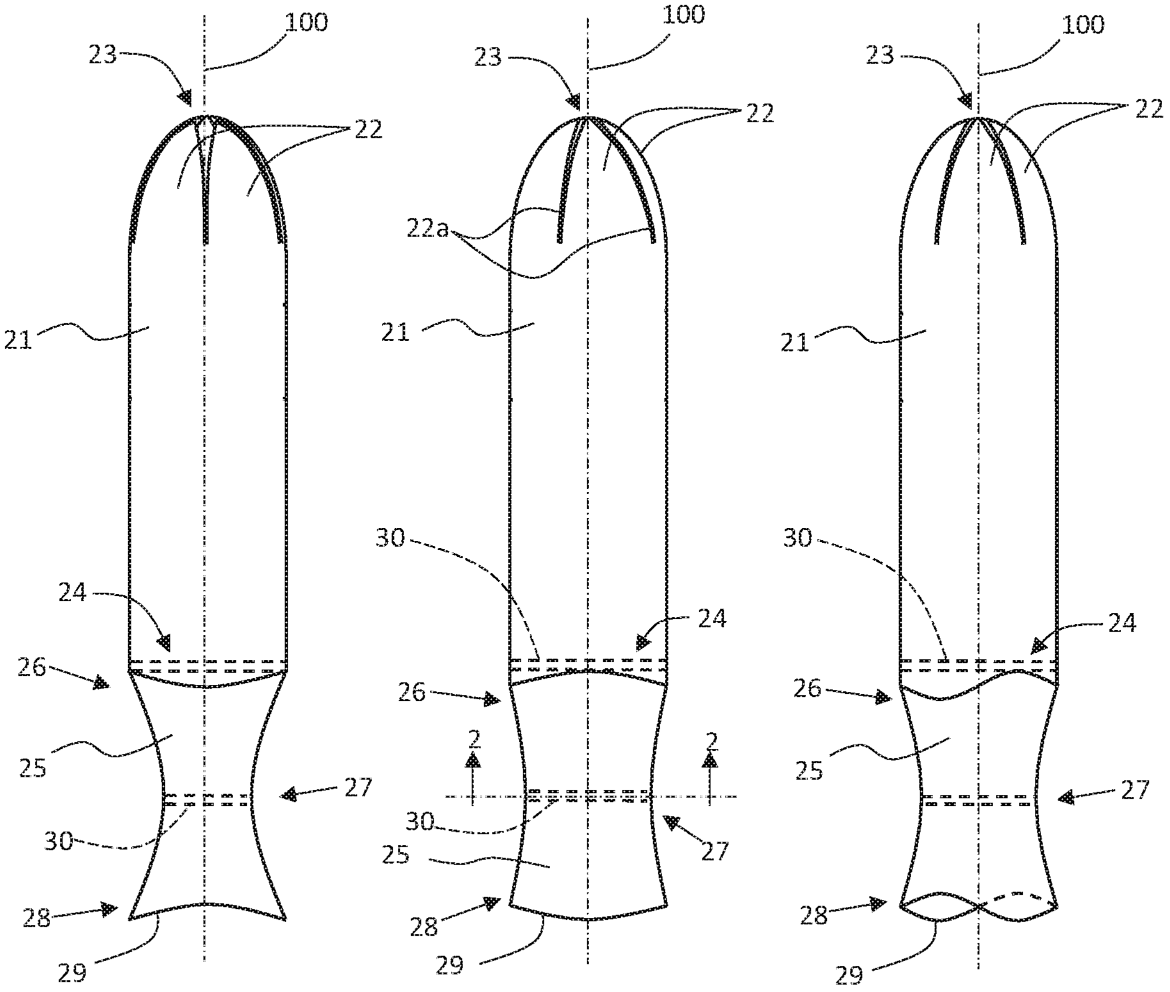
FIG. 1A is a longitudinal side view of the barrel and gripping portions of an applicator assembly in a first rotational orientation about its longitudinal axis.
FIG. 1B is a longitudinal side view of the barrel and gripping portions shown in FIG. 1A, in a second rotational orientation about its longitudinal axis 90 degrees from the first rotational orientation.
FIG. 1C depicts is a longitudinal side view of the barrel and gripping portions shown in FIG. 1A, in a third rotational orientation about its longitudinal axis 45 degrees from the first rotational orientation.
Figure 2:
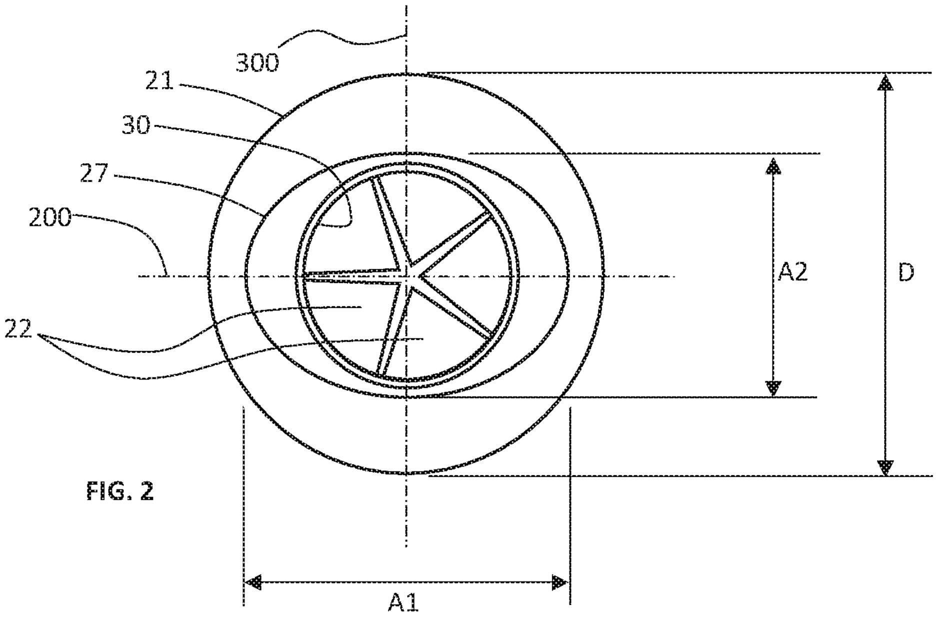
FIG. 2 is a lateral cross section of the barrel and gripping portions as shown in FIG. 1B, taken through line 2-2 in FIG. 1B.
Figure 3A:
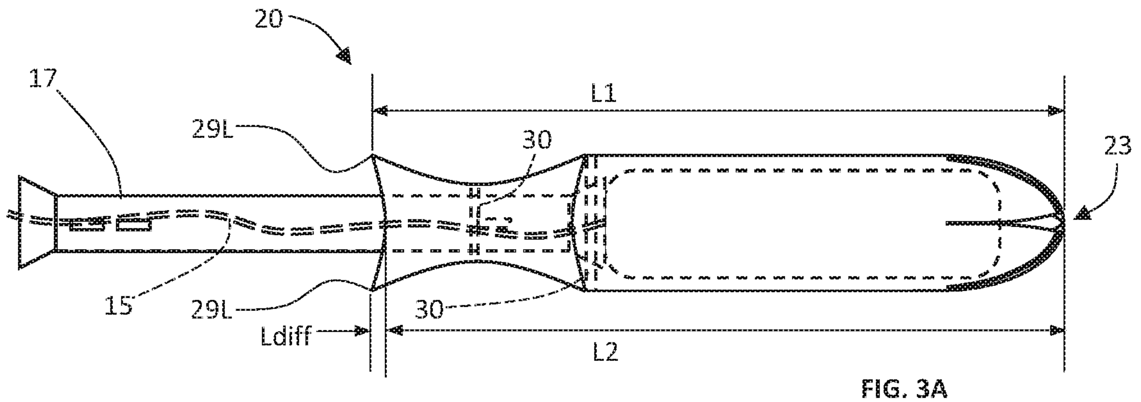
FIG. 3A is a longitudinal side view of an applicator assembly containing a tampon, in a first rotational orientation about its longitudinal axis, prior to ejection of the tampon.
Figure 3B:
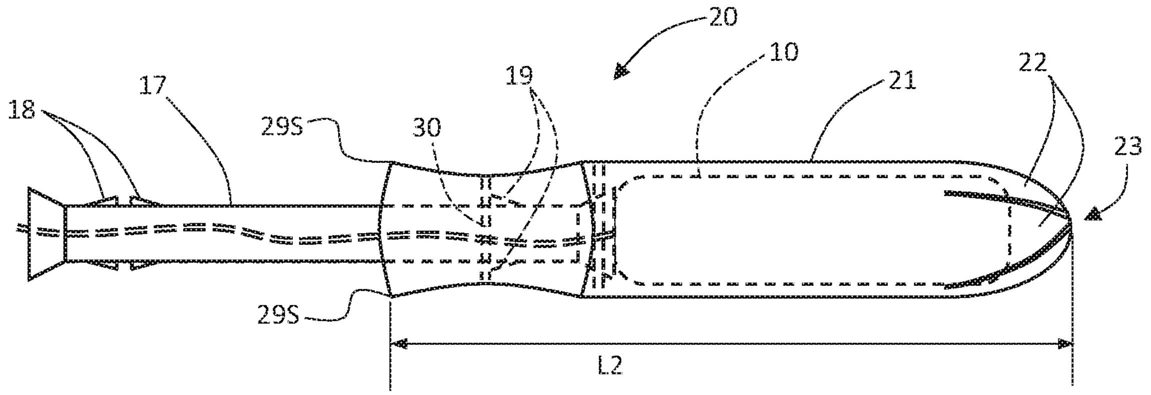
FIG. 3B is a longitudinal side view of an applicator assembly containing a tampon, in a second rotational orientation about its longitudinal axis 90 degrees from the first rotation, prior to ejection of the tampon.
Figure 4A:
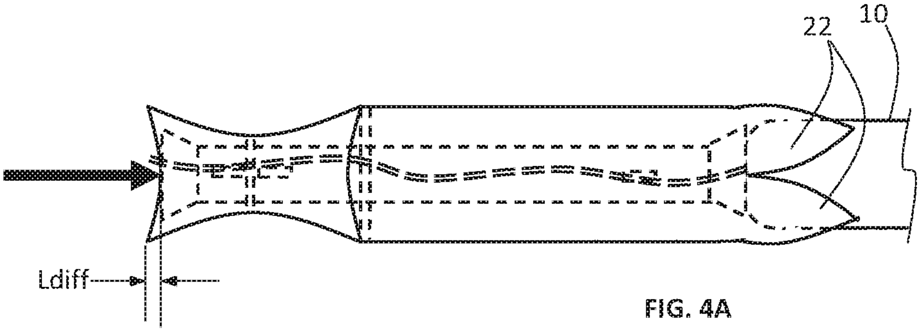
FIG. 4A is a longitudinal side view of an applicator assembly containing a tampon, in a first rotational orientation about its longitudinal axis, with the plunger portion pushed into the barrel portion and near completion of ejection of the tampon.
Figure 4B:
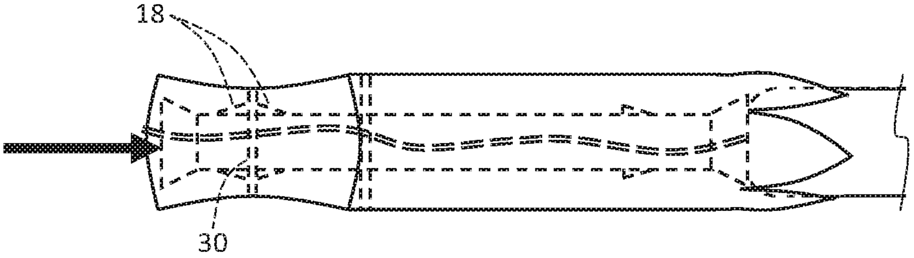
FIG. 4B is a longitudinal side view of an applicator assembly containing a tampon, in a second rotational orientation about its longitudinal axis 90 degrees from the first rotation, with the plunger portion pushed into the barrel portion and near completion of ejection of the tampon.

The "longitudinal axis" of a tampon, or of a barrel portion of an applicator assembly, is the line along the normal direction of insertion of the tampon and applicator by a user, through the geometric center of a cross section profile of the tampon or barrel portion, where the cross section lies along a plane perpendicular to the normal primary direction of insertion. The longitudinal axis of an example of the barrel portion of an applicator assembly is illustrated in FIGS. 1A-1C.

"Lateral" with respect to a tampon or applicator assembly refers to a direction perpendicular to its longitudinal axis. "Width" refers to a dimension measured along a direction perpendicular to the longitudinal axis.

"Longitudinal" with respect to a tampon or applicator assembly refers to a direction parallel to its longitudinal axis. "Length" refers to a dimension measured along a direction parallel to the longitudinal axis.

"Axial" movement of an element means movement along the longitudinal axis of an element. An "axial" direction is parallel to the longitudinal direction.

"Coaxial" refers to the movement of an ejection plunger within a barrel portion of an applicator assembly, whereby the plunger moves within the barrel portion and substantially along and/or parallel to its longitudinal axis.

"Vaginal cavity" refers to the internal body cavity of a human female, extending between the introitus of the vagina (sometimes referred to as the opening or sphincter of the vagina) and the cervix.

Tampon Construction

Typically, a tampon is manufactured of one or more absorbent materials, which have been assembled, cut, shaped and compressed in one or both of the lateral direction and the axial direction, in order to provide a body of a size and stability of form when dry to allow for neat insertion into a user's vaginal cavity. Components, assembly methods, and precompression configurations and shapes may vary among manufacturers and/or manufacturing processes. A new tampon has a forward (insertion) end and a rearward (withdrawal) end. When housed in an applicator assembly, the forward end is proximate the forward (insertion) end of the barrel portion of the applicator assembly, proximate the petals (when included) of the barrel portion. Tampons intended for placement in the vaginal cavity to absorb menstrual fluid during menses often have a substantially cylindrical compressed shape prior to application. Preferably, a tampon will substantially retain its compressed shape and size as long as it is kept dry, prior to insertion and use. The pre-application shape and size need not persist following insertion and during use. Tampons typically expand in size and change shape in varying ways during use, as they are contacted by and absorb fluid.

Tampons also may be manufactured and formed to have other shapes and forms, as described in, for example, U.S. Pat. Nos. 6,824,536; 6,932,805; 8,597,267; 8,684,987; 8,216,202; 6,953,456; 6,554,814; 7,549,982; 6,939,340, and 8,029,485.

The tampon may be a non-layered, uniform structure, or it may be a laminar structure comprised of integral or discrete layers, or the tampon may have a folded structure, or it may be rolled, or any other suitable structure known in the art. Generally, it may be preferred that the tampon have a certain minimal rigidity when new and dry, to facilitate ejection from an applicator assembly and/or insertion, by pushing on the rearward end.

The tampon may be constructed from a variety of liquid-absorbing materials commonly used in absorbent articles, such as, for example, rayon, cotton, or comminuted wood pulp (which is generally referred to as airfelt). Examples of other suitable absorbent materials include creped cellulose wadding; formations including meltblown filaments spun from polymeric resin, including coformed formations; chemically stiffened, modified or cross-linked cellulosic fibers; synthetic fibers such as crimped polyester fibers; peat moss; absorbent foams; tissue including tissue wraps and tissue laminates; or any other suitably absorbent material or combination or blend of absorbent materials. Preferred absorbent materials include cotton and rayon (including tri-lobal and conventional rayon fibers, and needle punched rayon). Suitable types of rayon may include GALAXY rayon (a tri-lobal rayon fiber structure) available as from Kelheim Fibres GmbH of Kelheim, Germany, and TENCEL rayon (a round fiber rayon) available from Lenzing AG, Lenzing, Austria. Suitable cotton material includes, long fiber cotton, short fiber cotton, cotton linters, T-fiber cotton, card strips, and comber cotton. Additionally, superabsorbent materials, such as superabsorbent polymers or absorbent gelling materials in particle or fiber form may be incorporated into the tampon.

The absorbent material(s) of the tampon may be surrounded by an overwrap. The overwrap is preferably a liquid permeable material. Such materials may include knitted, woven or nonwoven fabrics of rayon, cotton, fibers spun from polymeric resins, including bicomponent fibers, or any other suitable natural or synthetic fibers known in the art. Rayon, polyethylene, polypropylene and blends of these are particularly suited for use as overwrap material. Synthetic fibers may include fibers spun or formed of polyester, polyolefin, nylon, polypropylene, polyethylene, polyacrylic, cellulose acetate, or combinations of these, such as bicomponent fibers. Natural fibers or semi-synthetic fibers may include fibers of cotton or rayon. In general, cotton and/or rayon fibers may be preferred for inclusion because they provide ready absorption and fluid wicking. Synthetic (polymer-based) fibers may also be preferred for inclusion for their surface characteristics and properties to balance the capillarity of more absorbent materials included, and enable the tampon to more readily slip against moist tissue, resulting in easier and more comfortable tampon insertion and removal. The overwrap may be adapted or formed to extend rearwardly beyond the rearward end of the assembly of absorbent material(s) to form a skirt portion, as described in U.S. Pat. No. 6,840,927, for example. The overwrap may be configured to extend from about 2 mm to about 30 mm beyond the rearward end of the assembly of absorbent material(s).

The tampon may include a withdrawal cord, which may be attached to or along any portion of the tampon. This may be any type of withdrawal cord known in the art, for example a generally braided (or twisted) withdrawal cord. A conventional type of withdrawal cord (in terms of thickness, material composition, etc.) may be periodically braided with a thicker slub of fibrous material, which acts as a wicking member, to form a structure to be connected to the remaining of the tampon. In such an embodiment, the portion of the cord, which will act as the withdrawal cord, may be treated to make it non-absorbent or even hydrophobic. It may also be a withdrawal cord as described in commonly assigned and co-pending U.S. application Ser. No. 09/309,467.

The tampon may contain any additional functional ingredients, such as antimicrobial agents, lubricants, antioxidants, pH modifiers, etc., as known in the art.

It may be preferred in some circumstances that the tampon may comprise a chevron-shaped (laminar) pad, prior to compression into a substantially cylindrical form. This pad may be formed to have a lateral width and a longitudinal length wherein the width is greater than the length. The pad may include at least three layers of absorbent material, including an uppermost layer, a lowermost layer, and at least one intermediate layer positioned between the uppermost layer and lowermost layer. Each of the uppermost layer and the lowermost layer may be formed primarily of rayon, and the at least one intermediate layer may be formed primarily of cotton.

Applicator Assembly

A tampon may be provided new within an applicator assembly, configured to contain the tampon until use, and then to facilitate insertion of the tampon without the need to insert a finger into the vaginal cavity to push the tampon into position. An applicator assembly having a barrel and plunger arrangement may be preferred. Barrel and plunger portions may be formed of molded polymer resin, paper, or other suitable material, or a combination thereof. It may be desirable in some circumstances that one or more components of the assembly be translucent or transparent to allow the user to view the tampon or a feature thereof within the assembly, for example, to determine whether the assembly contains a tampon (i.e., has not been used), or to observe features of the tampon. In some circumstances it may be desired that the material(s) forming the applicator be tinted or pigmented to impart a non-white color for esthetic purposes and/or to reduce visibility of menstrual fluid that may be deposited thereon following use. In some circumstances it may be desired that one or more components of the applicator assembly be substantially opacified, or opacified and tinted or pigmented.

The applicator assembly manufactured so as to be flushable as described in U.S. Pat. No. 6,730,057. The applicator assembly may be corrugated as described in U.S. Pat. No. 7,066,870. The applicator assembly may be provided with a gripping portion as described in U.S. Pat. Nos. 8,303,558; 7,081,110; 8,449,491, or U.S. Pat. No. 8,075,512. The applicator assembly may be provided with an absorbency indicator as described in U.S. Pat. No. 7,166,101.

The applicator assembly may be provided with a cap and/or insertion tip portion that allows for a smooth and safe insertion of the assembly. A rupturable cap may be provided as described in U.S. Pat. No. 6,610,025, that will protect the tampon from contamination prior to use, but will rupture and allow the tampon to be pushed forward and out of the applicator assembly when the user desires to do so. The cap be formed of or include flexible or movable petals as described in U.S. Pat. No. 6,652,477.

Referring now to FIGS. 1A-1C, 2, 3A, 3B, 4A and 4B, an applicator assembly 20 may include a barrel portion 21, a gripping portion 25 and an ejection plunger 17.

Barrel portion 21 may include an approximately or substantially tubular and hollow section which may also include a substantially cylindrical outer shape, have a forward end 23 and a rearward extent 24 and may be sized and proportioned to snugly contain a compressed tampon 10, while serving as a vehicle for facilitating comfortable delivery of the tampon to a suitable location within the vaginal cavity. In some examples barrel portion 21 may have a lateral cross section profile that is substantially circular; in other examples it may have a lateral cross section outer profile that is oval-shaped, ovoid-shaped, stadium-shaped or elliptical. Barrel portion 21 may have a forward/insertion end portion formed by a group of radially-arranged, flexible petals 22 defined by slots 22*a* therebetween as suggested in the figures. Petals 22 may be shaped and rounded radially inwardly as they approach the forward end 23, as suggested in the figures, to neatly form a smoothly tapering, rounded forward/insertion end portion/tip to facilitate easy and comfortable insertion. In some examples petals 22 may be integral extensions of the barrel portion 21, molded or otherwise heat-formed with a rounded taper as suggested in the figures.

Gripping portion 25 may have a forward portion 26, an intermediate portion 27, a rearward portion 28 and a rearward edge 29. As suggested in FIGS. 1A-1C, gripping portion 25 may have a shape that transitions from a larger lateral dimension where it joins barrel portion 21, to a smaller lateral dimension at intermediate portion 27, and flaring to a larger lateral dimension at rearward portion 28. This provides a tactilely-perceivable portion at which the user can intuitively, comfortably and ergonomically grip the applicator assembly with opposing fingers, to manipulate the applicator assembly to insert a tampon. In some examples the gripping portion 25 may be provided or formed with a rubberized surface, or a surface having increased tack or increased coefficient of friction with human skin relative the barrel portion surface, or surface finish, textural features, or surface topographic features (which may include esthetic/decorative elements) or any combination of these features (not specifically shown), for gripping slip resistance. When such features are provided on the gripping portion 25 but are absent on a majority of the outer surface area of the barrel portion 21, such features may provide further tactile and/or visible means of identification of the gripping portion to the user.

Textural or topographic features on the surface may be both functional, for gripping slip resistance, and decorative, for esthetic appeal. Gripping portion 25 may be integrally molded or formed with barrel portion 21, or may be separately formed and then joined to barrel portion 21 via fusion/welding, thermal bonding, adhesive bonding, chemical bonding or other suitable bonding mechanism, or may be joined to the barrel portion via cooperating, interlocking physical/mechanical features. For purposes of efficient manufacture and structural integrity, it may be preferred that gripping portion 25 be integrally formed with/joined to barrel portion 21. Barrel portion 21 may be formed of any suitable material having suitable surface properties that provide for substantial non-absorption of body fluids (i.e., during the brief time of insertion and withdrawal in normal use) and low friction against moist tissue, to provide for ease and comfort of insertion and withdrawal. In some examples barrel portion 21 may be formed of a cardboard or paperboard tube, having an outer coating (e.g., of a wax or polymer) to provide for non-absorption and low friction. In other examples barrel portion 21 may be formed of a polymeric resin. In more particular examples barrel portion 21 may be formed of injection-molded polymeric resin predominately constituted by polyethylene, which has suitable low surface friction characteristics. In particular examples barrel portion 21 and gripping portion 25 may be integrally injection molded together.

Preferably, the majority of the outside surface area of the barrel portion 21 is provided with a smooth and/or glossy surface finish, to provide for low friction with tissues during use. In contrast, the gripping portion may be provided with a matte (or rougher) surface finish and/or any combination of the above-described features for enhancing gripping slip resistance.

To further enhance rapid visual and/or tactile identifiability of the gripping portion, the gripping portion and the barrel portion may be provided with visibly differing/contrasting colors; visibly differing levels of opacity/transparency/translucency; visibly/tactilely differing surface finishes, visibly/tactilely differing/contrasting surface textural features, tactilely differing/contrasting structural stiffness (e.g., gripping portion 25 is formed with thicker walls relative the barrel portion walls, resulting in a relatively, stiffer gripping portion structure that may be tactilely perceived), or any combination thereof. Additionally, or in combination, the respective barrel and gripping portions 21, 25 may be formed of or include respectively differing component materials or formulations thereof, that impart any of the visibly and/or tactilely perceivable differences listed in the preceding sentence.

Referring to FIGS. 3A, 3B, 4A and 4B, an applicator assembly 20 may be provided with an ejection plunger 17, configured along with the barrel portion and gripping portion to fit and slide coaxially within the barrel portion and gripping portion. The ejection plunger 17 may be hollow and cylindrical. As such, in some examples, the ejection plunger can be hollow so as to provide a central axial space within which a withdrawal cord 15 attached to and extending rearward from tampon 10 may reside prior to use. In some examples, the ejection plunger 17 may have one or both ends flared as shown or otherwise formed to have relatively enlarged pushing surfaces, which contact the tampon 10 and user's pushing finger, during application, respectively.

In some examples, the ejection plunger 17 may include two coaxially-arranged sub-portions (not shown) wherein one sub-portion may slide coaxially within the other in telescope fashion, as described and depicted in US 2015/0060317. Such a configuration for the ejection plunger may be included to provide the advantages described in the cited reference.

The barrel portion 21 and/or gripping portion 25 may be provided with one or more internal plunger guides 30, to provide a relatively close internal tolerance between the ejection plunger 17 and the barrel and/or gripping portions 21, 25, at least two differing longitudinal positions within the barrel portion and/or gripping portion. Plunger guides 30 may be provided and suitably configured and sized to provide clearances that ensure that the plunger may effectively freely slide longitudinally therewithin, but be guided substantially linearly/coaxially through the gripping and barrel portions to efficiently eject the tampon 10 from barrel portion 21 during application. The ejection plunger 17 may be provided with one or more retainer structures 19 that cooperate with internal features of the barrel portion and/or the gripping portion (such as plunger guides 30) to prevent the plunger 17 from sliding out and away from the rear of the gripping portion. The plunger 17 also may be provided with one or more latching/detent structures 18 that cooperate with internal features of the barrel portion and/or the gripping portion (such as plunger guides 17) to latch the plunger 17 into a forward position following substantial ejection of the tampon 10, indicating that the applicator assembly has been used, and retaining the applicator (including the ejection plunger) in a more compact form for carrying and disposal following its use (as appears in FIGS. 4A and 4B).

Comparing FIGS. 3A and 3B and FIGS. 4A and 4B, it can be appreciated that flexible petals 22 can be formed and configured to flex about bases thereof at the barrel portion, radially outwardly from the longitudinal axis, spreading to create and/or enlarge an opening at the forward end of the applicator assembly, through which the tampon 10 can be ejected during application.

As may be appreciated from FIGS. 1A-1C and 2, gripping portion 25 may have additional features that enhance its utility. Gripping portion 25 may be configured to be visually and tactilely distinguishable from barrel portion 21 by a transition to a differing outer shape, size or geometry, at forward portion 26, the differing shape, size or geometry having one or more lateral dimensions that are smaller than a smallest lateral dimension of the barrel portion 21 proximate the forward portion 26. Barrel portion may include a substantially cylindrical portion having a circular lateral outer cross section profile having a diameter D. The transition may be gradual or abrupt. In the example depicted in the figures, in a first rotational orientation reflected in FIG. 1A, intermediate portion 27 may have its smallest lateral dimension, shown along minor axis 300 of its lateral cross section as dimension A2 in FIG. 2. In a second rotational orientation reflected in FIG. 1B (90 degrees from the first rotational orientation, rotated about longitudinal axis 100), intermediate portion 27 may have its largest lateral dimension, shown along major axis 200 of its lateral cross section as dimension A1 in FIG. 2. For example, a lateral cross section through the intermediate portion may have an outer profile that is non-circular. In various non-limiting examples, the lateral outer cross section profile may have, substantially, a rounded rectangle shape, an elliptical shape, an oval shape, an ovoid shape or a stadium shape. In some examples, the lateral outer cross section profile of the gripping portion may have a lateral cross section that is non-circular at the intermediate portion 27 but transitions smoothly from non-circular to circular, moving from intermediate portion 27 to forward portion 26 wherein it joins a substantially cylindrical barrel portion 21. In some examples, the outer profile of the gripping portion may have a lateral cross section that is non-circular through the intermediate portion 27 but transitions smoothly from non-circular to circular, moving from intermediate portion 27 to rearward portion 28 where it ends at rear edge 29. In some examples, the gripping portion 25 may be formed with an outer shape that at least partially defines a hyperbolic paraboloid.

Figure 6:
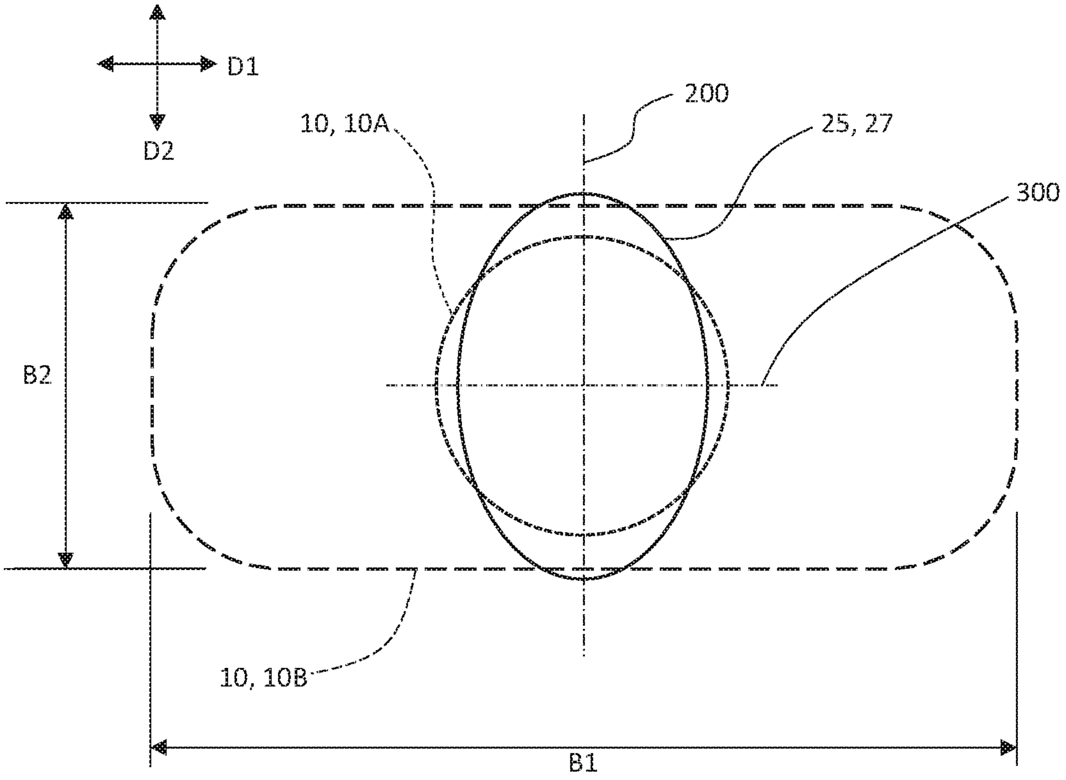
FIG. 6 is an illustration superimposing a lateral/cross-sectional outer profile of an example of a gripping portion (25) of an applicator assembly, with a lateral/cross-sectional outer profile of an example of a dry, compressed tampon (10, 10A) contained within an associated applicator assembly prior to use, and a lateral/cross-sectional outer profile of the same tampon (10, 10B) following application, absorption of fluid and resulting lateral expansion of the tampon along two directions.

This difference in lateral dimensions between rotational orientations of the gripping portion 25 may enhance its slip resistance and/or ergonomic feel. It also may serve to provide the user with a tactile indication of rotational orientation of the applicator assembly, which may be useful in examples in which the tampon within the barrel portion has directionality or differing shape or expansion features according to the tampon's rotational orientation. For example, referring to FIG. 6, a tampon having a dry, compressed shape and size 10A prior to application may be configured such that it expands laterally to a second shape and size 10B in use (as it absorbs fluid and swells) to a greater extent, to a greatest dimension B1, along a first lateral direction D1, compared with expansion laterally to a lesser dimension B2 along a second lateral direction D2 90 degrees from the first lateral direction. In some circumstances, being suitably configured for such directionality of expansion may make the tampon more effective for trapping and absorbing menstrual fluid, when inserted in a particular rotational orientation and suitable position within the user's vaginal cavity. The tampon may be disposed within the applicator assembly 20 in a particular rotational orientation about the longitudinal axis relative the rotational orientation of the gripping portion 25. In the non-limiting example illustrated in FIG. 6, the tampon may be disposed within the applicator such that the larger lateral dimension of the lateral profile of gripping portion 25 (e.g. along a major axis 200 thereof, at intermediate portion 27) is substantially perpendicular to the direction of greater expansion D1 of the tampon, and/or conversely, the tampon may be disposed within the applicator such that the smaller lateral dimension of the lateral profile of gripping portion 25 (e.g. along a minor axis 300 thereof, and at intermediate portion 27) is substantially parallel to the direction of greater expansion D1 of the tampon. It will be appreciated that this rotational orientation relationship may be reversed, as well, if preferred. The user may be provided with suitable accompanying information concerning such relative rotational orientation relationship between the tampon within the applicator and the gripping portion. Provided with this information the user may rely upon the above-described geometric features of the gripping portion 25 to visually and/or tactilely determine the rotational orientation of the tampon 10 within the applicator assembly 20, and be equipped to insert the tampon into the vaginal cavity in an optimally effective rotational orientation.

Figure 5:
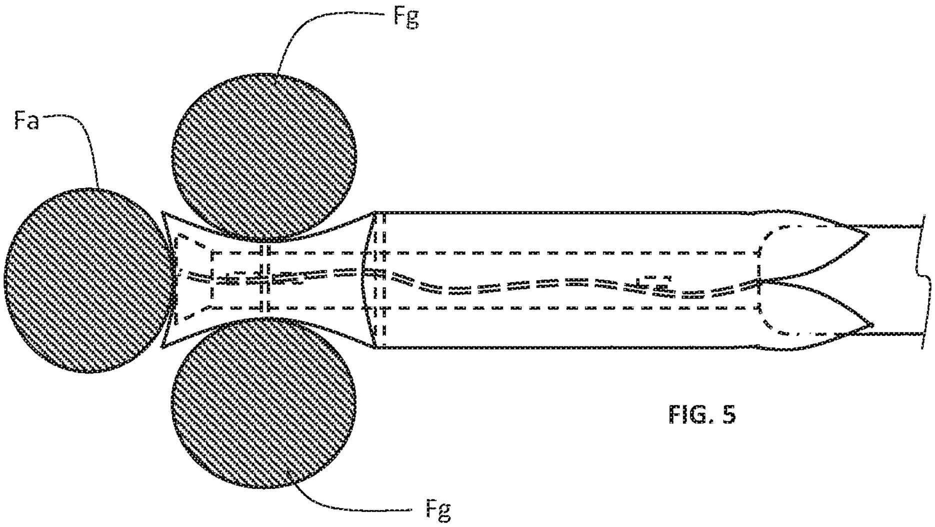
FIG. 5 is a longitudinal side view of an applicator assembly containing a tampon, in a first rotational orientation about its longitudinal axis, with the plunger portion pushed into the barrel portion and near completion of ejection of the tampon, schematically depicting potential user finger placement gripping and actuating the applicator assembly.

Additionally, gripping portion 25 may have an effectively greater length dimension along rearward edge 29 at one pair of opposing portions, and an effectively lesser length dimension along rearward edge 29 at a second, differing pair of opposing portions. For example, referring to FIGS. 3A, 3B and 4A, one pair of opposing portions 29L of the rear edge 29 of the gripping portion may extend rearward from the forward tip of the applicator to a relatively greater length L1, and a second pair of opposing portions 29S of rear edge 29 of gripping portion 25 may extend rearward from the forward tip of the applicator to a relatively lesser length L2. In some examples, these respective pairs of opposing portions may be disposed approximately 90 degrees from each other about the longitudinal axis of the applicator assembly. This provides a relatively greater length of the gripping portion, extending to length L1, for the user to grip the gripping portion, while the dip or recess in the rear edge 29 extending to lesser length L2 enables the user to depress ejection plunger 17 into the applicator assembly in an axial direction (marked by the large arrows in FIGS. 4A and 4B) by a depth that is greater than that which would be allowed if the gripping portion had the same length dimension about its entire rear edge 29. This greater depth is the difference between L1 and L2, designated Ldiff in FIGS. 3A and 4A. In the particular, non-limiting example depicted, greater length L1 lies along a longitudinal line that intersects and may be coplanar with the minor axis 200 of the intermediate portion lateral cross section (shown in FIG. 2), while lesser length L2 lies along a longitudinal line that intersects and may be coplanar with the major axis 300. This configuration may provide better ergonomic feel for the user's gripping and actuating fingers Fg and Fa, during use of the applicator assembly, as may be appreciated from FIG. 5. For example, gripping fingers Fg may be a thumb and middle finger of one hand, and actuating finger Fa may be a forefinger of the same hand. It will be appreciated that the dimension Ldiff may be increased or decreased as may be desired through configuration of the shapes and profiles of gripping portion 25 and of rear edge 29.

In view of the foregoing description, the following non-limiting examples are contemplated:

1. A tampon product comprising a tampon (10) within an applicator assembly (20), the applicator assembly comprising:

a hollow barrel portion (21) having a longitudinal axis (100), the barrel portion having a forward end (23) and a rearward extent (24);

a hollow gripping portion (25), the gripping portion having a forward portion (26) joined to the rearward extent (24), an intermediate portion (27), and a rearward portion (28) terminating at a rearward edge (29), wherein:

the forward portion (26) comprises a transition from a first lateral outer cross section profile of the barrel portion (21) at the rearward extent (24) to a second lateral outer cross section profile of the intermediate portion (27) of the gripping portion (25) differing from the first lateral outer cross section profile; and the barrel portion (21) and the gripping portion (25) together have a first length (L1) from the forward end (23) to the rearward edge (29) at a first portion (29L);

the barrel portion (21) and the gripping portion (25) together have a second length (L2) from the forward end (23) to the rearward edge (29) at a second portion (29S); and the second length is less than the first length.

2. The tampon product of example 1 wherein the barrel portion (21) comprises at least in part a substantially cylindrical outer shape, having a substantially circular lateral outer cross section profile having a diameter (D).

3. The tampon product of either of examples 1 or 2, wherein the barrel portion (21) has a first lateral dimension at the rearward portion (24), and the gripping portion (25) has a second lateral dimension (A1, A2) at the intermediate portion (27) that is less than the first lateral dimension.

4. The tampon product of any of examples 1-3 wherein the second lateral outer cross section profile is substantially oval-shaped, ovoid-shaped, elliptical or stadium-shaped and has major (200) and minor (300) axes, each perpendicular to the longitudinal axis (100).

5. The tampon product of example 4 wherein the second lateral outer cross section profile has greater (A1) and lesser (A2) lateral dimensions along the major (200) and minor (300) axes, respectively, and at least one of the greater and lesser lateral dimensions is less than a greatest measurable lateral dimension of the first lateral outer cross section profile of the barrel portion (21) at the rearward extent (24).

6. The tampon product of example 5 where the first length (L1) is measurable at a location along the rearward edge (29) at a point that lies within a plane defined by the longitudinal axis (100) and the major axis (200).

7. The tampon product of example 5 where the second length (L2) is measurable at a location along the rearward edge (29) at a point that lies within a plane defined by the longitudinal axis (100) and the minor axis (300).

8. The tampon product of any of examples 3-7 wherein the gripping portion (25) comprises an outer surface at least partially defining a hyperbolic paraboloid.

9. The tampon product of any of the preceding examples wherein the first length (L1) is the greatest measurable length of the barrel portion and the gripping portion combined.

10. The tampon product of any of the preceding examples wherein the second length (L2) is the smallest measurable length of the barrel portion and the gripping portion combined.

11. The tampon product of any of the preceding examples wherein the tampon (10) is configured such that, following its ejection from the applicator assembly and absorption of fluid, it will expand laterally to a first tampon lateral dimension (B1) to a greatest extent along a first lateral direction (D1), and to a lesser second tampon lateral dimension (B2) along a second lateral direction (D2) 90 degrees from the first lateral direction.

12. The tampon product of either of examples 4 or 5 wherein the tampon (10) is configured such that, following its ejection from the applicator assembly and absorption of fluid, it will expand laterally to a first tampon lateral dimension (B1) to a greatest extent along a first lateral direction (D1), and to a lesser second tampon lateral dimension (B2) along a second lateral direction (D2) 90 degrees from the first lateral direction; and the first lateral direction (D1) is substantially parallel to one of the major (200) and minor (300) axes, preferably substantially parallel to the minor axis (300).

13. The tampon product of either of examples 11 or 12 further comprising associated information directed to a user, concerning a relative rotational orientation relationship between the tampon (10) within the applicator (20), and the shape of the gripping portion (25).

14. The tampon product of any of the preceding examples wherein the first length (L1) occurs at two oppositely disposed locations along the rearward edge (29).

15. The tampon product of any of the preceding examples wherein the second length (L2) occurs at two oppositely disposed locations along the rearward edge (29).

16. The tampon product of any of the preceding examples wherein first length (L1) and second length (L2) occur at respective locations along the rearward edge (29) that are 90 degrees apart, relative the longitudinal axis (100).

17. The tampon product of any of the preceding examples further comprising an ejection plunger (17), wherein the barrel portion (21), the gripping portion (25) and the ejection plunger are sized and configured such that the ejection plunger may slide inside the gripping portion and the barrel portion.

18. The tampon product of example 16 wherein the barrel portion (21) and/or the gripping portion (25) comprise an internal plunger guide (30) configured to contact the ejection plunger (17) and guide the ejection plunger along a sliding path within the gripping portion and the barrel portion that is coaxial with the longitudinal axis (100).

19. A tampon product comprising a tampon (10) within an applicator assembly (20), the applicator assembly comprising:

a hollow barrel portion (21) having a longitudinal axis (100), the barrel portion having a forward end (23) and a rearward extent (24);

a hollow gripping portion (25), the gripping portion having a forward portion (26) joined to the rearward extent (24), an intermediate portion (27), and a rearward portion (28) terminating at a rearward edge (29), wherein:

the forward portion (26) comprises a transition from a first lateral outer cross section profile of the barrel portion (21) at the rearward extent (24) to a second lateral outer cross section profile of the intermediate portion (27) of the gripping portion (25) differing from the first lateral outer cross section profile;

the second lateral outer cross section profile is substantially oval-shaped, ovoid-shaped, elliptical or stadium-shaped and has major (200) and minor (300) axes, each perpendicular to the longitudinal axis (100); and wherein the tampon (10) is configured such that, following its ejection from the applicator assembly (20) and absorption of fluid, it will expand laterally to a first tampon lateral dimension (B1) to a greatest extent along a first lateral direction (D1), and to a lesser second tampon lateral dimension (B2) along a second lateral direction (D2) 90 degrees from the first lateral direction; and wherein the first lateral direction (D1) is substantially parallel to one of the major (200) and minor (300) axes, preferably substantially parallel to the minor axis (300).

20. The tampon product of example 19 wherein the barrel portion (21) comprises at least in part a substantially cylindrical outer shape, having a substantially circular lateral outer cross section profile having a diameter (D).

21. The tampon product of either of examples 19 or 20, wherein the barrel portion (21) has a first lateral dimension at the rearward portion (24), and the gripping portion (25) has a second lateral dimension (A1, A2) at the intermediate portion (27) that is less than the first lateral dimension.

22. The tampon product of any of examples 19-21 wherein the second lateral outer cross section profile has greater (A1) and lesser (A2) lateral dimensions along the major (200) and minor (300) axes, respectively, and at least one of the greater and lesser lateral dimensions is less than a greatest measurable lateral dimension of the first lateral outer cross section profile of the barrel portion (21) at the rearward extent (24).

23. The tampon product of any of examples 19-22 wherein the gripping portion (25) comprises an outer surface at least partially defining a hyperbolic paraboloid.

24. The tampon product of any of examples 19-23 further comprising associated information directed to a user, concerning a relative rotational orientation relationship between the tampon (10) within the applicator, and the shape of the gripping portion (25).

25. The tampon product of any of examples 19-24 further comprising an ejection plunger (17), wherein the barrel portion (21), the gripping portion (25) and the ejection plunger (17) are sized and configured such that the ejection plunger (17) may slide inside the gripping portion (25) and the barrel portion (21).

26. The tampon product of example 25 wherein the barrel portion (21) and/or the gripping portion (25) comprise an internal plunger guide (30), preferably a plurality of internal plunger guides (30), configured to contact the ejection plunger (17) and guide the ejection plunger (17) along a sliding path within the gripping portion (25) and the barrel portion (21) that is coaxial with the longitudinal axis (100).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" where a small deviation would be functionally equivalent.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon product comprising a tampon within an applicator assembly, the applicator assembly comprising:

- a hollow barrel portion having a longitudinal axis, the barrel portion having a forward end and a rearward extent;
- a hollow gripping portion, the gripping portion having a forward portion joined to the rearward extent, an intermediate portion, and a rearward portion terminating at a rearward edge, wherein:
  - the barrel portion and the gripping portion together have a first length from the forward end to the rearward edge at a first portion thereof;
  - the barrel portion and the gripping portion together have a second length from the forward end to the rearward edge at a second portion thereof;
  - the barrel portion and the gripping portion together have a third length from the forward end to the reward edge at a third portion thereof;
  - the barrel portion and the gripping portion together have a fourth length from the forward end to the reward edge at a fourth portion thereof;
  - the first length is equal to the third length and the second length is equal to the fourth length;
  - the first portion is opposite the third portion and the second portion is opposite the third portion; and
  - the second length is less than the first length,
  - wherein the gripping portion has a first lateral dimension that is perpendicular to the longitudinal axis, wherein the first lateral dimension has a major axis and a minor axis, wherein the major axis is greater than the minor axis,
  - where the first length is measurable at a location along the rearward edge at a point that lies within a plane defined by the longitudinal axis and the minor axis,
  - where the second length is measurable at a location along the rearward edge at a point that lies within a plane defined by the longitudinal axis and the major axis,
  - wherein the barrel portion comprise an internal plunger guide configured to contact an ejection plunger,
  - wherein the plunger comprises one or more latching structures that are configured to cooperate with the internal plunger guide,
  - wherein the tampon exhibits a directionality of expansion comprising greater expandability in a first lateral tampon direction than in a second lateral tampon direction, and
  - wherein the first lateral tampon direction is substantially aligned with the major axis of the first lateral dimension of the gripping portion to provide a tactile indication of the directionality of expansion.

2. The tampon product of claim 1, wherein the barrel portion has a second lateral dimension at the rearward portion, and the gripping portion has the first lateral dimension at the intermediate portion that is less than the second lateral dimension.

3. The tampon product of claim 1 wherein the second lateral outer cross section profile is substantially oval-shaped, ovoid-shaped, elliptical or stadium-shaped.

4. The tampon product of claim 3 wherein the second lateral outer cross section profile has greater and lesser lateral dimensions along the major and minor axes, respectively, and at least one of the greater and lesser lateral dimensions is less than a greatest measurable lateral dimension of the first lateral outer cross section profile of the barrel portion at the rearward extent.

5. The tampon product of claim 2 wherein the gripping portion comprises an outer surface at least partially defining a hyperbolic paraboloid.

6. The tampon product of claim 1 wherein first length and second length occur at respective locations along the rearward edge that are 90 degrees apart, relative the longitudinal axis.

7. The tampon product of claim 1 wherein the barrel portion, the gripping portion and the ejection plunger are sized and configured such that the ejection plunger may slide inside the gripping portion and the barrel portion.

8. A tampon product comprising a tampon within an applicator assembly, the applicator assembly comprising:

- a hollow barrel portion having a longitudinal axis, the barrel portion having a forward end and a rearward extent;
- a hollow gripping portion, the gripping portion having a forward portion joined to the rearward extent, an intermediate portion, and a rearward portion terminating at a rearward edge, wherein:
  - the forward portion comprises a transition from a first lateral outer cross section profile of the barrel portion at the rearward extent to a second lateral outer cross section profile of the intermediate portion of the gripping portion differing from the first lateral outer cross section profile;
  - the forward portion of the gripping portion is at least one of concave and convex;
  - the barrel portion and the gripping portion together have a first length from the forward end to the rearward edge at a first portion thereof;
  - the barrel portion and the gripping portion together have a second length from the forward end to the rearward edge at a second portion thereof;
  - the first length occurs at two oppositely disposed locations along the rearward edge;
  - first length and second length occur at two oppositely disposed locations along the rearward edge; and
  - the second length is less than the first length,
  - wherein the gripping portion has a lateral dimension that is perpendicular to the longitudinal axis, wherein the lateral dimension has a major axis and a minor axis, wherein the major axis is greater than the minor axis,
  - where the first length is measurable at a location along the rearward edge at a point that lies within a plane defined by the longitudinal axis and the minor axis,
  - where the second length is measurable at a location along the rearward edge at a point that lies within a plane defined by the longitudinal axis and the major axis,
  - wherein the barrel portion comprise an internal plunger guide configured to contact an ejection plunger and guide the ejection plunger along a sliding path within the gripping portion and the barrel portion that is coaxial with the longitudinal axis, wherein the plunger comprises one or more latching structures that are configured to cooperate with the internal plunger guide, wherein the tampon is configured to expand laterally to a first tampon lateral dimension to a greatest extent along a first lateral direction, and to a lesser second tampon lateral dimension along a second lateral direction 90 degrees from the first lateral direction; and the first lateral direction is substantially parallel to one of the major and minor lateral axes of the gripping portion to provide a tactile indication of the expansion.

9. A tampon product comprising a tampon within an applicator assembly, the applicator assembly comprising:

a hollow barrel portion having a longitudinal axis, the barrel portion having a forward end and a rearward extent;

a hollow gripping portion, the gripping portion having a forward portion joined to the rearward extent, an intermediate portion, and a rearward portion terminating at a rearward edge, wherein the forward portion comprises a transition from a first lateral outer cross section profile of the barrel portion at the rearward extent to a second lateral outer cross section profile of the intermediate portion of the gripping portion differing from the first lateral outer cross section profile, wherein the forward portion of the gripping portion is nonlinear, wherein the gripping portion comprises a first pair of opposing portions and a second pair of opposing portion, wherein the first pair of opposing portions have a first length from the forward end to the reward edge measured parallel to the longitudinal axis, wherein the second pair of opposing portion have a second length from the forward end to the reward edge measured parallel to the longitudinal axis, and wherein the first length is greater than the second length, wherein the gripping portion has a lateral dimension that is perpendicular to the longitudinal axis, wherein the lateral dimension has a major axis and a minor axis, wherein the major axis is greater than the minor axis, wherein the first length is measurable at a location along the rearward edge at a point that lies within a plane defined by the longitudinal axis and the minor axis, wherein the second length is measurable at a location along the rearward edge at a point that lies within a plane defined by the longitudinal axis and the major axis, wherein the barrel portion comprise an internal plunger guide configured to contact an ejection plunger and guide the ejection plunger along a sliding path that is coaxial with the longitudinal axis, wherein the plunger comprises one or more latching structures that are configured to cooperate with the internal plunger guide, wherein the tampon is configured to expand laterally to a first tampon lateral dimension to a greatest extent along a first lateral direction, and to a lesser second tampon lateral dimension along a second lateral direction 90 degrees from the first lateral direction; and the first lateral direction is substantially parallel to one of the major and minor lateral axes of the gripping portion to provide a tactile indication of the expansion.

* * * * *